United States Patent [19]
Bell et al.

[11] Patent Number: 4,661,071
[45] Date of Patent: Apr. 28, 1987

[54] VACUUM SINTERED POWDER ALLOY DENTAL PROSTHETIC DEVICE AND OVEN TO FORM SAME

[75] Inventors: A. Milton Bell, Teaneck; Murray G. Gamberg, Manalapan; Ronald Kurzeja, Bridgewater, all of N.J.

[73] Assignee: Denpac Corp., Hackensack, N.J.

[21] Appl. No.: 622,997

[22] Filed: Jun. 21, 1984

Related U.S. Application Data

[63] Continuation-in-part of Ser. No. 596,314, Apr. 3, 1984.

[51] Int. Cl.4 ................................................ A61C 5/10
[52] U.S. Cl. ................................. 433/223; 433/222.1; 427/2; 106/35
[58] Field of Search ............... 433/223, 222, 218, 219, 433/208, 202, 203, 201, 228, 9; 106/35; 427/2, 229; 75/228

[56] References Cited

U.S. PATENT DOCUMENTS 3,934,348  1/1976  Janjie ................................... 433/223
3,987,545  10/1976 Kennedy ............................... 433/36
4,181,757  1/1980  Youdelis .............................. 427/229
4,358,271  11/1982 Sperner et al. ....................... 433/201
4,426,404  1/1984  Shoher et al. ........................ 433/223
4,433,958  2/1984  Fellman et al. ...................... 433/199
4,468,251  8/1984  Hausselt et al. ..................... 433/219
4,501,613  2/1985  Matsumoto ............................ 75/228
4,527,979  7/1985  McLean et al. ....................... 433/9

Primary Examiner—John J. Wilson
Attorney, Agent, or Firm—Lackenbach Siegel Marzullo & Aronson

[57] ABSTRACT

An alloyed metal dental prosthetic device, such as a coping, of an alloy dental reconstructive element, is formed from a liquid phase sintered powdered metal alloy at elevated temperatures of about 1000°–1300° C. under a high level of vacuum of about 10 to 1000 microns of Hg. A special oven is devised which will achieve this high level of vacuum in a rapid efficient manner. The resultant metal prosthetic device has the density of at least that found in commercial cast prosthetic devices.

8 Claims, 5 Drawing Figures

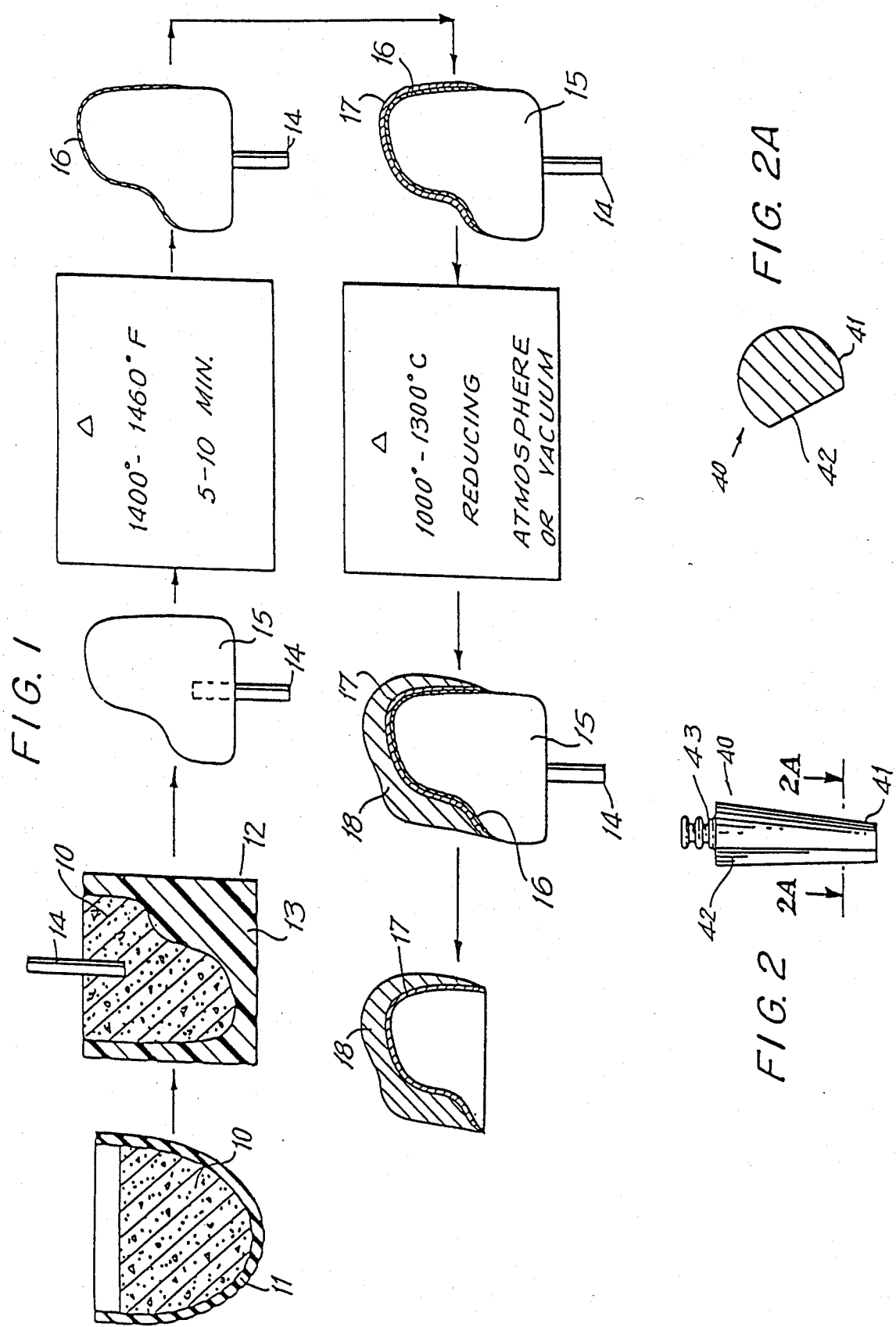

4,661,071

VACUUM SINTERED POWDER ALLOY DENTAL PROSTHETIC DEVICE AND OVEN TO FORM SAME

This application is a continuation-in-part application of Ser. No. 596,314, filed Apr. 3, 1984.

FIELD OF THE INVENTION

This invention relates to dental reconstructive elements, with particular reference to fixed and removable dental prostheses. Specifically this invention relates to alloy crowns and bridges, and to an oven for forming same.

BACKGROUND AND DISCUSSION OF THE PRIOR ART

The conventional state of the art for the construction of crowns and bridges for dentistry is largely dependent upon the lost wax technique, which requires the casting of molten metal into an investment material employed to preserve the original form of a wax pattern.

The wax pattern is formed and designed to precisely fit either a die or model which is a replica of the tooth part prepared by the dentist to receive the crown or bridge to be fabricated. The wax pattern is duplicated in an alloy as either a full cast crown, a veneer crown, or a thimble-like coping, pontic, inlay or onlay, to which porcelain may be baked and bonded to form the finished element.

A summary of the state of the art is as follows and as further discussed in the article, "The Ceramic-Metal Restoration", *Quintessence of Dental Technology*, October 1983, pp. 545-8, A. Milton Bell, D.D.S.

Various ceramic, metallic and ceramo-metal materials have been employed in attempts to improve crowns and bridges. Such materials are disclosed in U.S. Pat. No. 4,243,412, granted Jan. 6, 1981 to Jandon; U.S. Pat. No. 4,249,943 granted Feb. 10, 1981 to Mohammed, et al: U.S. Pat. No. 4,265,669, granted May 5, 1981 to Starling et al; U.S. Pat. No. 2,206,502, granted July 2, 1940 to Heiligman; U.S. Pat. No. 3,649,732, granted Mar. 14, 1972 to Brigham et al; U.S. Pat. No. 4,321,042 granted Mar. 23, 1982 to Scheicher; U.S. Pat. No. 2,106,809 granted Feb. 1, 1938 to Prange, et al; U.S. Pat. No. 3,450,545, granted June 17, 1969 to Ballard et al and U.S. Pat. No. 3,786,565 granted Jan. 22, 1974 to Jarrault. In general;

(1) The dentist prepares a tooth or teeth to be restored by one or more forms of fixed prosthodontic appliances dependent upon the nature of the restoration designed for the particular application (i.e. a crown, bridge, splint or partial denture.

(2) The dentist must then impression the prepared tooth or teeth in an accurate manner in order to permit the accurate duplication of the patient's teeth to be restored by crowns or bridges. With this model or replica the dentist supplies an accurate duplication of the patient's opposing arch and a bite registration in what is known as centric relation. Thus a highly accurate duplication of the prepared teeth and the maxillo-mandibular relationship is prepared in model form on which the prosthesis is to be fabricated. Even in the restoration of a single crown, the dentist must provide the technician with an accurate duplication of the adjacent teeth as well as the opposing teeth in order to permit the building of contact points and occluding contact points in rest position of the jaws as well as in masticatory movements.

(3) Since the final restoration of a crown or bridge must harmonize with the patient's dentition in appearance as well as function, the precise model permits the fabrication of a wax pattern to conform to a specific design for a dental element.

(4) The finished wax pattern is sprued and then removed from the die or model and connected to a sprue former using a precise system of waxes to insure complete cast of the metal in the casting process. Since the wax pattern is removed from the die or model to be invested, this is considered to be an indirect fabrication technique. It is important to note this because discrepancies may be introduced in an indirect technique due to distortion of the wax pattern in the removal from the die. The wax may distort in the investing process, and the wax and investment materials undergo contraction and expansion changes due to temperature changes during burn-out and casting and solidification of the molten metal during the cooling cycle.

(5) The sprued wax pattern is then invested in a gypsum type of material such as cristobalite or a phosphate-bonded high heat material, depending upon the type of metal being cast.

(6) The invested was pattern when set is placed into a burnout oven for a period of one and a half hours or more, depending upon the technique and metal being cast, and the manufacturers instructions of the particular investment used. Temperatures of the burn-out oven may range from 900° F. to 1600° F., and may involve one or more heat stages to insure maximum expansion of the investment to compensate for initial contraction during the setting of the investment. This expansion during the heating cycle varies and may be a cause for an improper fit of the final restoration, if not properly closely controlled. The burn-out procedure not only expands the investment in preparation for the casting of the molten metal, but is essential for the elimination of the wax thus leaving a void in the investment material or a mold of the eliminated wax pattern.

(7) It is customary to use a casting ring to contain the investment material around the wax pattern. Spacers are used to permit the expansion of the investment in the heating stage. This is an imprecise technique and can cause improper fit of the final casting. Some investment materials use a plastic or paper ring for the purpose of forming and containing the investment material for the casting procedure. The plastic or paper is burned off during the burn-out stage or removed after the investment has set. This allows for maximum expansion of the investment during the heating stage. The actual casting is done by placing the investment which was formed by some kind of device, or in a steel ring, into some type of casting apparatus after the burn-out stage. This permits the melting of the desired metal at the required temperature, and the molten metal is then forced into the mold in the hot investment either by centrifugal force, pressure or vacuum. Conventional dental ovens provide for maximum vacuum pressures of 26-29in. Hg, ie. about 60,000 microns Hg. These ovens were typically used as porcelain firing furnaces. There are various types of equipment for these different methods of making a casting. Once the cast has been completed, the metal and investment material must be allowed to cool.

(8) The casting can be recovered from the investment material by breaking out the casting from the investment. The casting is then cleaned of any remnants of the investment material.

(9) The sprues must then be cut off the crown, bridge or pontic and smoothed down. The casting must then be fitted back upon the original die. If the technique employed by the technician utilizes a gypsum die it may be difficult to seat the casting on the model without scraping or chipping the die. The ultimate fit on the tooth is therefore complicated for the dentist.

Miscasts and incomplete castings which fail to reproduce fine margins or parts of the original wax pattern, or poor fit of the casting due to shrinkage and expansion factors of the wax and investment materials is not uncommon. This may require repeating the entire procedure if the casting cannot be properly seated on the die or prepared tooth of the patient.

While dental bridges can either be cast in one piece or assembled from individual units, a more accurate fit is assured by assembly of the units of the bridge or splint from an index impression taken of the units seated in the mouth, which may insure complete placement of the castings upon the individual prepared teeth. This technique has been widely employed for many years, utilizing the precious alloys which are relatively simple to solder. The non-precious alloys employed today are more difficult to solder or braze due to their formation of high oxide layers on their surfaces when subjected to high temperatures during this process. This has led the dentist to prescribe having their technicians cast multiple unit bridges and splints in one piece to eliminate the necessity for soldering. There is some question as to the accuracy of fit of such long space prostheses being cast as one piece.

These long, labor intensive prior art techniques are costly as well as time consuming, and sometimes provide a questionable or inaccurate fit.

Now there is provided by the present invention a direct method for the preparation of crowns, which avoids many of the aforesaid prior art problems.

It is a principal object of the present invention to provide a direct method and resultant prosthetic product having a density equal to or greater than the indirect prior art cast prosthetic.

It is another principal object of the present invention to provide an apparatus for rapidly and accurately achieving the immedatly aforesaid object.

These objects, as well as other objects, will become apparent from the reading of the following description, the adjoined claim, and the accompanying drawings, in which:

BRIEF DESCRIPTION OF THE DRAWINGS

FIG. 1 is a schematic illustration of the process of the present invention;

FIG. 2 is a greatly enlarged side elevational view of an alumina dowel used in the present invention;

FIG. 2A is a sectional view taken along 2A—2A of FIG. 2;

SUMMARY OF THE INVENTION

Figure 3:
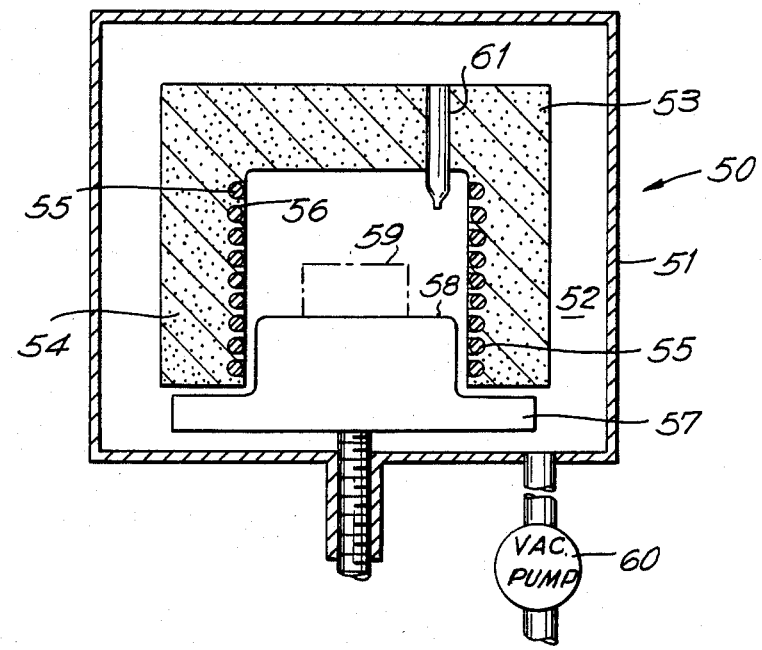
FIG. 3 is a schematic partial sectional view of a prior art dental oven.

A direct method for the formation of dental prosthetic elements having a metal component, such as a coping, full crown, pontic, inlay or partial denture, wherein the component is formed of a powdered metal liquid phase sintered alloy under a substantial vacuum of 10-1000 microns Hg, on a refractory die. The alloy is vacuum sintered to form an exact replica of the tooth surface and a porcelain may then be directly bonded to the formed element. An oven is designed to provide fast reliable vacuum sintering.

DESCRIPTION OF THE PREFERRED EMBODIMENTS

In a broad sense the present invention may be said to be a vacuum sintering process for forming a dental restorative element or appliance, such as a crown or bridge, having a liquid phase sintered powdered metal alloy coping. The invention also includes a novel oven design for achieving the requisite high levels of vacuum in a fast reliable manner. The metal alloy is sintered under vacuum pressures of about 10-1000 microns of Hg, and preferably 10-100 microns of Hg.

In another broad sense, the invention is a method for making the dental reconstructive or restorative element, which includes the following steps:

(a) forming an impression mold of a tooth surface so as to form a cavity replicating the prepared tooth surface.

(b) mixing a pourable refractory material;

(c) filling the cavity with said refractory material;

(d) separating the die from the mold;

(e) firing the refractory material to form a solid die, having a replicate of the tooth surface;

(f) covering the replicate surface with a powdered metal alloy;

(g) drawing vacuum to about 10 to 1000 microns Hg;

(h) sintering the alloy to form the metal component of the prosthetic element; and (i) bonding a restorative material to the metal.

A finished crown may not require bonding or retaining a restorative tooth material to the metal component to form said dental restorative element. That is where, for example, full cast crown or inlay or onlay is prepared, there is no need for adding restorative tooth material.

Refering now to FIG. 1, there is shown the detailed method of the present invention. A refractory die mixture 10 of colloidal silica MgO and kyanite is mixed in rubber vessel 11. The mixture 10 is then poured into an impression mold 12, and specifically the tooth replicate cavity 13. The impression mold may be formed from a plastic, rubber, wax or plaster. Before the mixture sets an alumina dowel 14 is placed into the mixture. After setting at room temperature, set mass or refractory die 15 replicating the tooth, is removed by dowel 14, and the die is then fired in a dental furnace to 1400° to 1460° C. for 5 to 10 minutes. The die expands, up to 3%, on firing. After firing and cooling a setting/release agent 16 is applied, and then a coating of a powdered metal alloy 17 is applied on the tooth replicating surface of the die. The coated die is then placed in a vacuum furnace and the alloy is liquid phase sintered at about 1000° to 1300° C., under high levels of vacuum to sinter the alloy. After the solid metal coping is formed, its outer surface is prepared for porcelain bonding and the porcelain 18 is bonded thereto.

A novel pourable refractory die material is used to replicate the tooth or teeth preparations as impressioned by the dentist, in order to construct the die or working model.

(1) The die material in addition to being a refractory material, is dimensionally stable to temperatures in excess of those temperatures required to sinter the powdered metal alloys designed for dental applications, which are generally in the range of 1000° to 1400° C. and preferably 1000° to 1300° C.

(2) The new refractory material is formed from a powder-liquid formulation and is mixed in a recommended ratio of powder to liquid so as to produce a pourable, easy flowing material. This reduces the possibility of bubbles. The refractory mass is easy to handle and sets in a relatively short time span permitting retrieval from the impression, with ease of initial trimming prior to firing.

(3) Most importantly, this new refractory die material has been designed to expand within controlled limits of up to 3%, and preferably 1-2% linear expansion, only upon the initial firing of the die (model) to compensate and allow for accurate fit of the final crowns or copings. Subsequent firings have no effect on the die material. The die material is not destroyed in the sintering process and enables the technician to then use the same die or refractory master model to support the frame or coping during the porcelain firing cycles. This insures greater accuracy of fit of bridges and splints with less chance of distortion or dimensional changes due to repeated firing cycles.

(4) This new refractory material is compatible with all types of dental alloys used in dentistry and designed for this process, (and may accept a separating medium or release agent which may prevent the metal from adhering to the die or model material).

The refractory die material is essentially a ceramic or mineral system with a specifically controlled expansion. Specifically the refractory die material is a combination of a specific aluminosilicate mineral ($Al_2SiO_5$), calcined magnesium oxide and colloidal silica. Preferably the aluminosilicate is kyanite. Other mineral systems contemplated include Alpha spodumene, and the like.

Solid components may be formulated as follows:
Kyanite—100 parts
Calcined magnesium oxide—0.05-0.2 parts The particle size of the kyanite should be in the range of minus 325 mesh. The calcined magnesium oxide is believed to promote gelation of colloidal silica when the liquid and solid components are combined.

The blended powder is mixed with sufficient colloidal silica to make the material a flowable suspension. The flowable suspension should be in the range of 25 ml./100 gm. to 30 ml./100 gm. (The colloidal silica is believed responsible for both the green and fired strength of the die). The suspension has approximately five minutes working time before it undergoes an initial set. This working time may be altered if desirable. The material continues to harden and should be allowed to bench-set for thirty to sixty minutes at which time it can be retrieved from the impression mold.

When fired at 1400° to 1460° C., the refractory material expands and the kyanite converts to mullite and free silica, upon firing.

After pouring, a special alumina dowel is inserted in the poured refractory molds. This special dowel can withstand the high sintering temperatures and multiple firings without interfering with the metal or porcelain fabrication procedures. The special dowel may be machined from a number of inert compatible materials, but the preferred material is a high alumina formulation.

Referring to FIG. 2, there is shown the preferred dowel 40. Dowel 40 comprises a tapered cylindrical body 41 with keyed flat 42, and a machined undercut 43 for retention in the refractory material. Dowel 40 is formed so as to permit fitting to accomodate different lengths for the height of the master model, and can be machined to large, medium and small sizes in order to accomodate the larger dies duplicating the molar preparations, medium for bicuspids, and smaller sizes for lower anterior or upper lateral incisor dies.

When pouring the refractory material into the dental impression, the alumina dowel is placed and fixed into position. (After the initial set the die may be removed from the impression and trimmed.) The die is then reseated into the impression in such a fashion so that a master model can be constructed which would permit the die to be removed and reseated by use of the dowel which acts as an accurate seating key. The die and model are then removed from the impression and the die is separated from the model and fired to 1400° to 1460° C. to achieve expansion. The characteristics of this system is unique in that most ceramic systems can then be mounted on some form of articulator and the technician can build the metal restoration with the powdered metal alloy as described herein below.

While the components named herein are the preferred materials for the formulation described for the process, other additives and components can give similar satisfactory results. For instance, another mineral which manifests an expandable property upon firing is alpha-spodumene. This might be used in place of kyanite. Generally any cation can be used to promote gelation in colloidal silica. Magnesium oxide is particularly desirable because of its high melting point. Liquid binders other than colloidal silica which yield similar results may be substituted such as ethyl silicate and monoammonium phosphate are also contemplated.

Another most important aspect of the present invention is the vacuum sintered liquid phase powdered alloy. That is, the specifically tailored powdered metal alloy forms a hardened mass on the refractory die by liquid phase vacuum sintering. This liquid phase vacuum sintering is particularly desirable because of the rapid densification without pressing. In the powdered alloy system, the firing temperature is above the melting point of one alloy but below the melting point of the other alloy.

The terms "sintered liquid phase powder metal alloy" as used hereinbefore and hereinafter, are understood to mean and contemplate both single and multiple powder metal alloy systems.

Suitable powdered metal alloy systems include the Ni-Cr alloys the Au-Pd, Cr-Co and Ag-Pd alloys, and more specifically including Ni-Cr-Mo-Al and Ag-Pd-Sn-In alloys. High gold and high palladium alloy systems, as well as other dental compatible alloys are possible.

It is important to note that the alloy system of the present invention can be selected so that its coefficient of thermal expansion matches that of the crown material. Where the crown material is porcelain, the thermal coefficient of expansion of the alloy desirably matches that of the porcelain. This match is at $13-14 \times 10^{-6}$/in-/in/°C. at 575° C.

It is also within the contemplation of the invention to use a wetting and release/separating medium or agent on the refractory die material to enhance the removal of the sintered powdered alloy, particularly so for the fitting or try-in phase by the dentist. The refractory die is also preferred for holding the crown during the porcelain baking step.

The powdered alloy should be about 90 microns or less, and in general, sintered at temperatures from 1000°–1400° C. and preferably 1000°–1300° C., but this may vary depending upon the specific alloy system. It is most preferred that there be a range of particles sized between about 5 to 90 microns, to insure dense packing for vacuum sintering. Sintering should be carried out in a high level of vacuum of 10 to 1000 and preferably 10 to 100 microns of Hg, so as to avoid oxidation of the metals at elevated temperatures, and more importantly to provide a high density or reduced porsity equal to or better than that achieved by conventional casting.

Referring to FIG. 3, there is a typical prior art dental oven 50. Oven 50 is formed with an outer housing 51 which in effect provides a vacuum chamber 52. A muffler 53 is disposed within the vacuum chamber 52. Muffle 53 is formed of a thick fibrous insulatory material 54 with heating elements 55 disposed at the inner circumferential surface 56. A reciprocating base 57 having a specimen platform 58 for mounting specimen 59, reciprocates in relationship to muffle 53 so as to enclose the specimen 59 for direct heating by elements 55. A vacuum pump 60 is operably connected to the outer housing 51. Pump 60 and housing 51 are designed to achieve maximum vacuum pressures of about 60,000 microns of Hg. The use is primarily for porcelain bonding operations. A thermocouple 61 completes the assembly.

Figure 4:
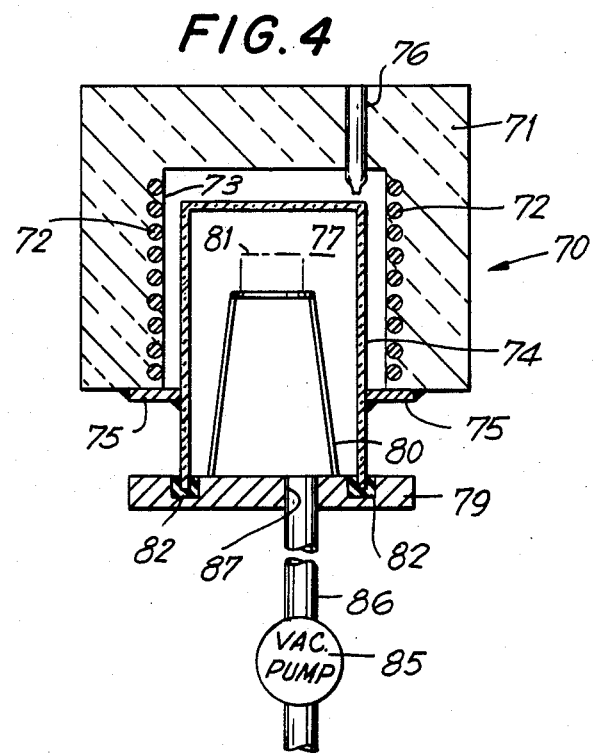
FIG. 4 is a schematic partial sectional view of the dental oven of the present invention.

Referring to FIG. 4 there is shown the oven of the present invention 70. Oven 70 is formed of an outer insulated member 71 having heating elements 72 disposed on the inner cylindrical surface 73. A non-fibrous alumina or mullite muffle or inverted cup 74, of ¼ to ⅜ inch thickness, is disposed on the inside of heating elements 72. Cylindrical inverted cup 74 is fixedly connected to member 71 by well known structural elements 75. Thermocouple 76 is mounted through member 71 and cup 74 for measuring the temperature within chamber 77. The assembly of 71 and 74 is mounted to well known reciprocating means (not shown) for the vertical reciprocation of this assembly for purposes hereinafter immediately appearing. A base 79 is provided with a mounting platform 80 disposed thereon for supporting a dental prosthetic preform 81. Annular seal 82 is provided on base 79 for providing a vacuum seal between cup 74 and base 79 when the assembly is vertically lowered to mate with the base. Vacuum pump 85 is mounted immediately adjacent the fixed base 79 and interconnected to chamber 77 by conduits 86 and 87. Pump 85 is capable of drawing a maximum of 0.1 micron Hg.

In this manner of construction there is a rapid accurate high vacuum maintained between 10 to 1000 microns Hg, and preferably 10 to 100 microns Hg. The close fixed mounting of the vacuum pump to the chamber permits a fast accurate high level of vacuum to be maintained. In addition the non-fibrous thin alumina cup 74 permits rapid high vacuum without breakdown of a fibrous structure. The thin alumina cup also permits rapid indirect heating of the preform within the chamber.

The following Examples are illustrative of the invention:

EXAMAPLE I

This example follows the method set forth in FIG. 1.

An impression of the tooth is taken by the well known technique. A final mixture of 27.5 ml. of colloidal silica (40% solids) amd 100 grams of the blended powder comprised of about 100 gm. of a powdered ceramic kyanite and 0.1 gm. calcined MgO is prepared in a container. The mixture is then vibrated into the cavity and an alumina dowel is inserted into the mixture. The mixture is allowed to set at room temperature for about 30 to 60 minutes. The die is then removed, trimmed, placed back and set into the impression. A master model is then constructed. The die and model are then removed from the impression. The die is then separated form the model and placet into the furnace and fired to 1400° C. for 10 minutes.

A powdered metal alloy system combining equal amounts of Ni-Cr (80:20) and Ni-Cr-Si (71:19:10) is prepared.

The powdered alloy system is mixed with propylene glycol to the consistency of heavy cream to paste, and then applied in an up to 10 mm coating on the wetted die surface. The propylene glycol is then dried off. The coated die is then fired in a furnace at 1275° C. to form the solid alloy component.

It is to be understood that while the description has been generally referred to in terms of the restorative dental element being a tooth, other elements such as portions of the maxillae or mandible are also contemplated as being part of the invention.

EXAMPLE II

To demonstrate the critical nature of the high vacuum level to achieve commercial levels of density, two samples (I and II) were prepared by the liquid phase sintering of a Ni:B:Si powdered metal alloy. The weight percentages of these components were 3.03% B, 4.6% Si and the balance Ni, measured on a binder-free basis. The binder was an iso-paraffinic hydrocarbon added to a paste consistency to provide a self-supporting preform. The powdered metal particle size range and distribution is shown below in the Table I. Samples I and II were fired at 930°–960° C. Sample I was sintered under 10–95 microns Hg, whereas Sample II was sintered under about 1000 microns Hg. This was the only difference in processing Samples I and II.

Metallographic specimens of each Sample were prepared and 200x photomicrographs on 3½"×5" photo prints of ASA 100 Kodacolar 35 mm film were made. Photocopies of each of the prints were then made and the photocopies weighed. Those portions of the photocopies that represented pores or voids were cut-out, and the "cut-out" photocopies were then weighed. The percentage porosity was then determined in accordance with the formula of footnote 2 of Table I.

A metallographic test sample was made of a standard Ag-Pd commercial dental casting, and the percent porosity determined by the aforesaid method. The comparative results are tabulated in Table I. T,0170

It has thus been demonstrated that commercial grade levels of porosity of about less than 1.50% can be achieved at vacuum levels of 10–95 microns Hg. In point of fact porosities of less than 1.00% are achieved at that vacuum level. That is the present invention provides a reduced porosity or density equal to or greater than commercial levels of dental castings.

Thus there has been shown a novel direct approach to obtain a dental crown or bridge through the use of the expandable refractory die and the liquid phase sintered powdered metal alloy coping.

The novel method and oven now permit direct rapid formation of a permanent prosthetic while the patient waits. This method can be accomplished in no more than about 1½ hours.

While we have described herein certain embodiments of our invention, we intend to cover as well any change or modification therein that may be made without departure from its spirit and scope.

We claim:

1. A method for forming a dental restorative element comprising:
   (a) forming an impression of a surface;
   (b) mixing a refractory material;
   (c) filling the impression with said refractory material to form a die preform;
   (d) separating the die preform from the impression;
   (e) firing the refractory material to form a solid die having a replicate of the surface;
   (f) covering the surface replicate with a powdered metal alloy;
   (g) drawing vacuum to 10 to 1000 microns Hg;
   (h) firing the alloy to sinter the alloy in the liquid phase to form a component of the element.

2. The method of claim 1, wherein step (g) is at about 10 to 100 microns Hg.

3. The method of claim 1, wherein step (h) is at 1000° C. to 1400° C.

4. The method of claim 1, said formed component having a porosity less than about 1.50%.

5. The method of claim 1, said formed component having a porosity less than about 1.00%.

6. The method of claim 1, where the powdered metal of step (f) comprises particulates of from 5 to 90 microns.

7. The method of claim 1 wherein the powdered metal of step (f) comprises particles from about 5 to about 90 microns in size and a binder to make a paste as a self-supporting preform.

8. The method of claim 7, wherein the component of the element is permanent and is formed in less than about 1½ hours.

* * * * *